(12) United States Patent
Luce

(10) Patent No.: US 9,320,430 B2
(45) Date of Patent: Apr. 26, 2016

(54) OPHTHALMIC DIAGNOSTIC INSTRUMENT AND METHOD

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 1500 days.

(21) Appl. No.: 12/751,281

(22) Filed: Mar. 31, 2010

(65) Prior Publication Data

US 2011/0245649 A1    Oct. 6, 2011

(51) Int. Cl.
*A61B 3/16* (2006.01)
*A61B 3/00* (2006.01)

(52) U.S. Cl.
CPC .............. *A61B 3/165* (2013.01); *A61B 3/0025* (2013.01)

(58) Field of Classification Search
USPC ........... 600/401, 515, 323, 330, 405; 351/237
See application file for complete search history.

(56) References Cited

U.S. PATENT DOCUMENTS

| | | | |
|---|---|---|---|
| 5,092,341 A | 3/1992 | Kelen | |
| 5,092,343 A | 3/1992 | Sptizer et al. | |
| 5,279,300 A * | 1/1994 | Miwa et al. | 600/401 |
| 5,307,096 A * | 4/1994 | Baroth et al. | 351/212 |
| 5,497,448 A | 3/1996 | Maruno et al. | |
| 5,630,019 A | 5/1997 | Kochi | |
| 5,701,907 A | 12/1997 | Klammer | |
| 5,751,911 A | 5/1998 | Goldman | |
| 5,769,074 A | 6/1998 | Barnhill et al. | |
| 5,776,069 A | 7/1998 | Platt | |
| 5,978,727 A | 11/1999 | Jones et al. | |
| 6,135,966 A | 10/2000 | Ko | |
| 6,208,983 B1 | 3/2001 | Parra et al. | |
| 6,386,706 B1 | 5/2002 | McClure et al. | |
| 6,658,287 B1 | 12/2003 | Litt et al. | |
| 6,839,581 B1 | 1/2005 | El-Solh et al. | |
| 7,130,835 B2 | 10/2006 | Cox et al. | |
| 2003/0088169 A1 | 5/2003 | Percival et al. | |
| 2004/0002639 A1 * | 1/2004 | Luce | 600/398 |
| 2004/0002640 A1 * | 1/2004 | Luce | 600/399 |
| 2004/0046936 A1 * | 3/2004 | Iwanaga | 351/212 |
| 2004/0183998 A1 * | 9/2004 | Luce | 351/212 |
| 2005/0030473 A1 * | 2/2005 | Fahrenkrug et al. | 351/200 |
| 2006/0281983 A1 | 12/2006 | Al-Ali et al. | |
| 2007/0173713 A1 | 7/2007 | Falck, Jr. et al. | |
| 2008/0071151 A1 * | 3/2008 | Sogin et al. | 600/301 |

(Continued)

OTHER PUBLICATIONS

Golebiowski et al.; Corneal mechanical sensitivity measurement using a staircase technique; Ophthal. Physiol. Opt., 2005, vol. 25; pp. 246-253.

(Continued)

*Primary Examiner* — Sean Dougherty
(74) *Attorney, Agent, or Firm* — Hodgson Russ LLP

(57) ABSTRACT

In an ophthalmic instrument that directs a fluid pulse at a cornea to cause reversible deformation of the cornea and monitors the corneal deformation to generate a deformation signal, the shape of the deformation signal is analyzed with respect to deformation signal data from a statistical population of eyes to calculate a deformation signal score indicating a degree of probability that the deformation signal corresponds in shape to a normal deformation signal for normal eyes in the population. In calculating the deformation signal score, significant geometrical signal parameters are calculated and combined. The deformation signal score may be used as a basis to keep or discard intraocular pressure measurements in a non-contact tonometer, and/or as a basis to conduct further diagnostic screening.

18 Claims, 9 Drawing Sheets

(56) References Cited

U.S. PATENT DOCUMENTS

2009/0271155 A1* 10/2009 Dupps et al. .................... 703/1
2011/0118585 A1* 5/2011 Ishii et al. .................... 600/401

OTHER PUBLICATIONS

Luce; Determining in vivo biomechanical properties of the cornea with an ocular response analyzer; J Cataract Refract Surg, 2005, vol. 31; pp. 156-162.

Luce; ORA Waveform Analysis and beyond; American Society of Cataract and Refractive Surgery, Apr. 3, 2009 Slide Presentation; 35 pages.

Murphy et al.; A new non-contact corneal aesthesiometer (NCCA); Ophthal. Physiol. Opt., 1996, vol. 16, No. 2; pp. 101-107.

WIPO; Written Opinion of the International Searching Authority for PCT/US2011/029706 dated May 7, 2011; 5 pages.

* cited by examiner

OPHTHALMIC DIAGNOSTIC INSTRUMENT AND METHOD

FIELD OF THE INVENTION

The present invention relates generally to ophthalmic instruments, and more particularly to ophthalmic instruments, for example non-contact tonometers, operable to cause and monitor a reversible deformation of the cornea.

BACKGROUND OF THE INVENTION

In the field of ophthalmic instruments, non-contact tonometers are well known for measuring intraocular pressure. Early non-contact tonometers, such as that introduced by Bernard Grolman in U.S. Pat. No. 3,585,849, measured intraocular pressure by directing an increasing force air pulse at the cornea to deform the cornea inward from an original convex state through a first flattened or "applanated" state to a concave state, and allowing the cornea to return outward from the concave state through a second applanated state to its original convex state with disintegration of the air pulse. Deformation of the cornea was monitored by an infra-red emitter and detector arranged on opposite sides of a test axis aligned with the cornea, such that the detector would receive light after reflection by the cornea and generate a signal characterized by first and second signal peaks corresponding to the moments of inward and outward applanation. The deformation signal was analyzed in conjunction with an increasing ramp signal of force-versus-time associated with generation of the air pulse by a solenoid-driven pump mechanism, whereby the time interval required to achieve inward applanation was used as a correlate of intraocular pressure.

Taking advantage of improvements in miniaturized sensor technology, more recent non-contact tonometers have abandoned reliance on a time interval correlate, and instead provide a pressure sensor within a plenum chamber of the pump mechanism to directly measure plenum pressure as a function of time during corneal deformation. The pressure signal from the pressure sensor is analyzed with the opto-electronically obtained deformation signal to determine intraocular pressure. See, for example, U.S. Pat. No. 7,481,767 to Luce.

The observation that a pressure differential exists between a plenum pressure associated with inward or first applanation and a pressure associated with outward or second applanation (referred to as "corneal hysteresis") has led to improvements in the accuracy of the intraocular pressure measurement and derivation of supplemental information about biomechanical characteristics of the corneal tissue. In this regard, see U.S. Pat. Nos. 6,817,981; 6,875,175; 7,004,902; and 7,481,767.

Nevertheless, it has long been recognized that a series of intraocular pressure measurements on a given eye will vary due to variability in the physical measurement process, such as slight differences in alignment of the instrument relative to the eye and randomly timed blinking by the test subject. Consequently, it has been accepted practice to perform a plurality of measurements on a given eye and to average the results. Also, it is known to discard what are perceived to be "outlying" intraocular pressure values from a set of measurements on an eye prior to averaging the remaining intraocular pressure measurement values.

Historically, the corneal deformation signal has always been analyzed in conjunction with a second metric, either a time interval or plenum pressure, to determine intraocular pressure and/or biomechanical characteristics of the corneal tissue. The corneal deformation signal has never been analyzed independently to yield information about the eye or about the physical measurement process giving rise to corneal deformation.

SUMMARY OF THE INVENTION

The present invention provides an ophthalmic apparatus and method for testing an eye of a patient.

The apparatus generally comprises a fluid pump for directing a fluid pulse at the eye to reversibly deform the cornea, a deformation detection system monitoring the corneal deformation and generating a deformation signal representing the corneal deformation as a function of time, signal processing electronics that converts the deformation signals from analog to digital form, and a processing unit programmed and configured to calculate a deformation signal score indicating a degree of probability that the deformation signal corresponds in shape to a normal deformation signal for a population of normal eyes. The deformation signal score may be used as a basis to keep or discard intraocular pressure measurements in a non-contact tonometer, and/or as a basis to conduct further diagnostic screening.

In an embodiment of the invention, the fluid pump is operable to generate and discharge the fluid pulse at the cornea to deform the cornea from an original convex state through a first applanated state to a concave state, wherein the cornea returns from the concave state through a second applanated state to the original convex state as the fluid pulse dissipates. The deformation detection system includes an emitter and a photosensitive detector arranged on opposite sides of the eye such that the detector receiving light from the emitter after the light is reflected by the cornea and generates the deformation signal. The deformation signal is filtered and converted by signal processing electronics from analog to digital form, and passed to the processing unit. The processing unit executes stored programming instructions to calculate the aforementioned deformation signal score. The deformation signal score may be computed by combining a plurality of signal parameters calculated by the processing unit, each signal parameter describing a respective geometrical property of the deformation signal.

The eye-testing method of the present invention generally comprises the steps of reversibly deforming the cornea of the eye from an original convex state through a first applanated state to a concave state, wherein the cornea returns from the concave state through a second applanated state to the original convex state; generating a deformation signal representative of the corneal deformation as a function of time; and calculating a deformation signal score indicating a degree of probability that the generated deformation signal corresponds in shape to a normal deformation signal for a population of normal eyes.

According to one embodiment, the invention may be implemented as an improvement to a non-contact tonometer, wherein a deformation signal score is calculated in conjunction with measuring intraocular pressure of the eye such that a plurality of deformation signals are generated each having a respective deformation signal score, wherein at least one of the plurality of deformation signals is kept or discarded based on its corresponding deformation signal score.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
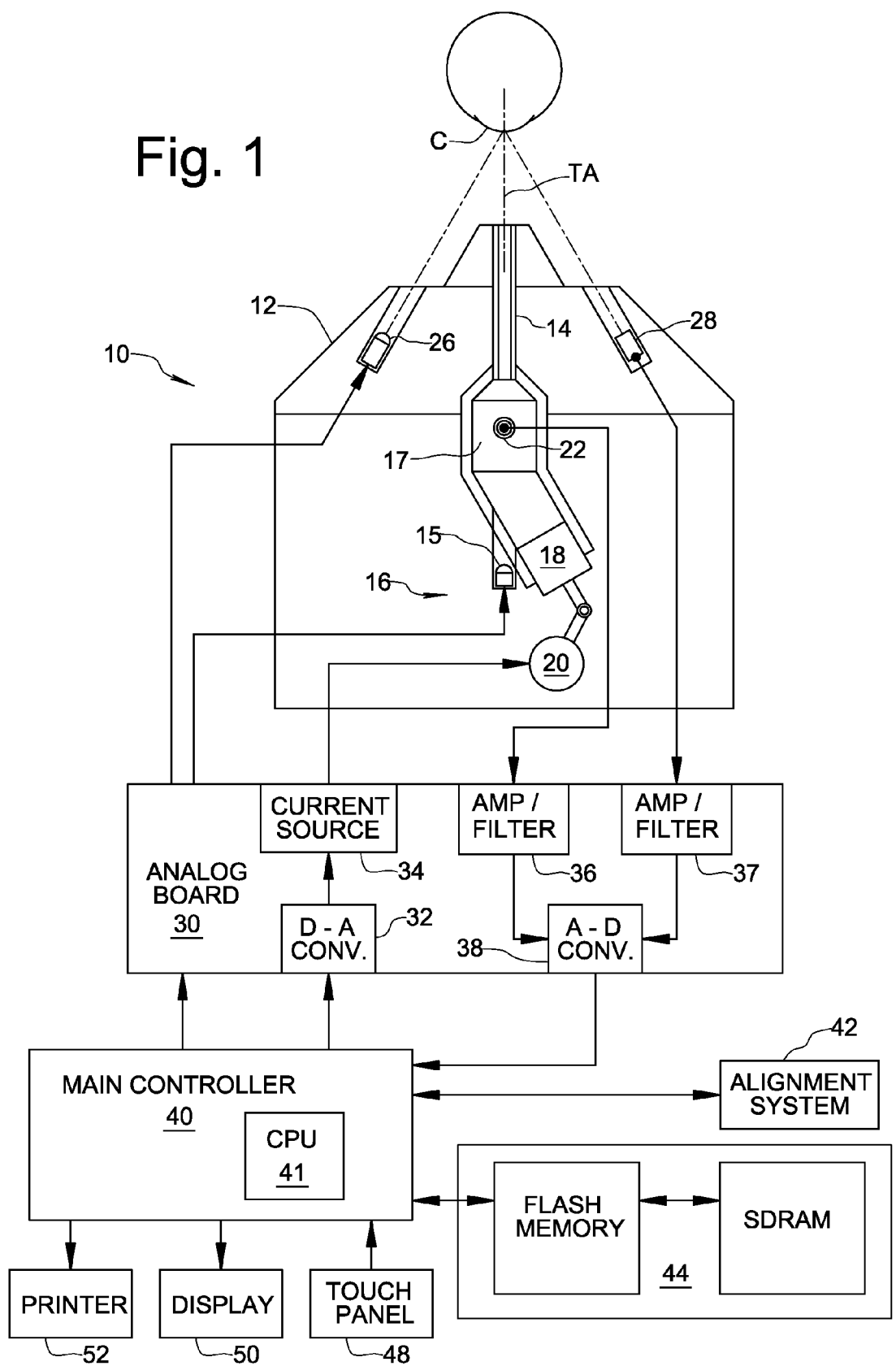
FIG. 1 is a schematic view of an ophthalmic apparatus formed in accordance with an embodiment of the present invention.

FIG. 1 schematically shows an ophthalmic apparatus 10 formed in accordance with the present invention for testing an eye of a test subject. As will be understood, apparatus 10 may be embodied in a non-contact tonometer ("NCT") that measures intraocular pressure ("IOP") by directing a fluid pulse at the cornea to deform the cornea. NCTs operating in this manner are already well known in the art of ophthalmic instruments.

A test portion of apparatus 10 is depicted as generally including a nosepiece 12 in which a fluid discharge tube 14 is fixed. The fluid discharge tube 14 defines a test axis TA that is aligned with a vertex of cornea C when measurement is carried out. The test portion of NCT 10 further includes a pump mechanism 16 having a plenum chamber 17 in flow communication with an entry end of fluid discharge tube 14, a piston 18 movable to compress fluid within plenum chamber 17, and a drive motor 20, such as a rotary solenoid, connected to piston 18. As will be familiar to persons skilled in the art of non-contact tonometry, the pump mechanism 16 is operable to rapidly increase fluid pressure within plenum chamber 17, thereby generating a fluid pulse that is discharged from an exit end of fluid discharge tube 14 in the direction of cornea C to cause reversible deformation of the cornea. In the depicted embodiment, a digital main controller 40 determines when fluid discharge tube 14 and test axis TA are within an acceptable three-dimensional alignment condition relative to cornea C based on information from an automated opto-electronic X-Y-Z alignment system 42 (the test subject is instructed to gaze at a fixation LED 15). When alignment is achieved, main controller 40 sends serial data to a digital-to-analog converter 32 connected to a current source 34 on an analog board 30, whereby current source 34 energizes drive motor 20 according to a predetermined current profile dictated by the serial data in order to generate a fluid pulse.

Suitable non-contact tonometers for practicing the present invention include, but are not limited to, the ATP Auto Non-Contact Tonometer/Pachymeter, the OCULAR RESPONSE ANALYZER®, and the Reichert 7 Auto Tonometer all manufactured by Reichert, Inc., assignee of the present application.

Figure 2A:
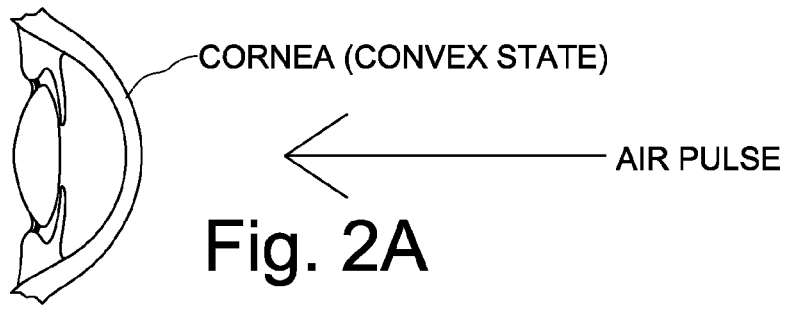
FIGS. 2A-2E are a series of figures depicting reversible deformation of a cornea associated with operation of the ophthalmic apparatus shown in FIG. 1.
Figure 2B:
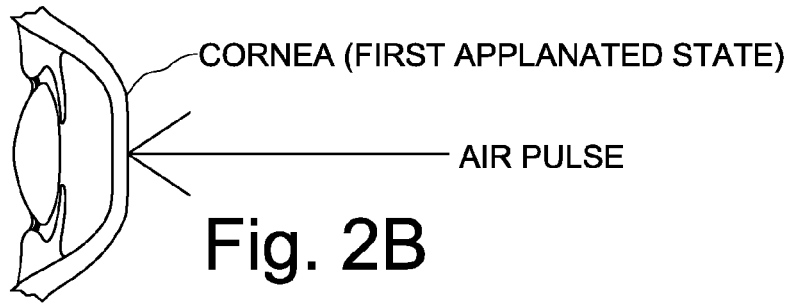
Figure 2C:
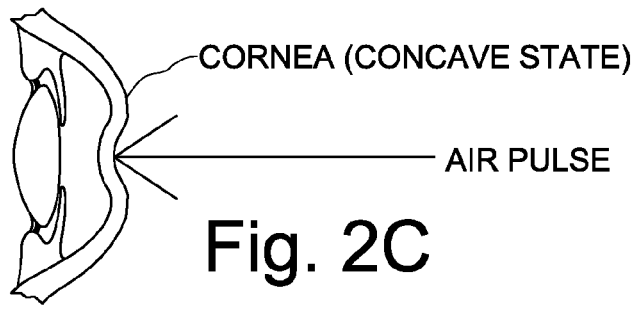
Figure 2D:
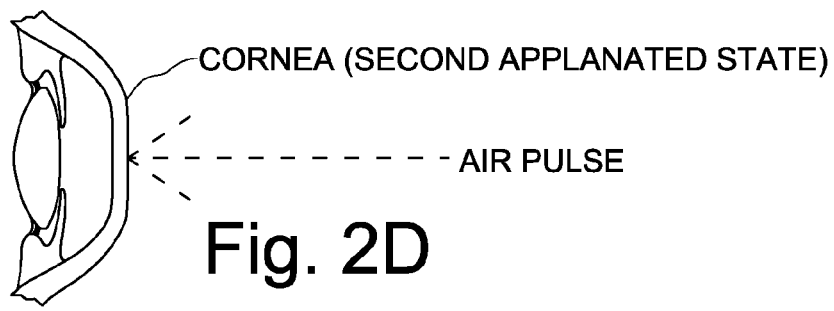
Figure 2E:
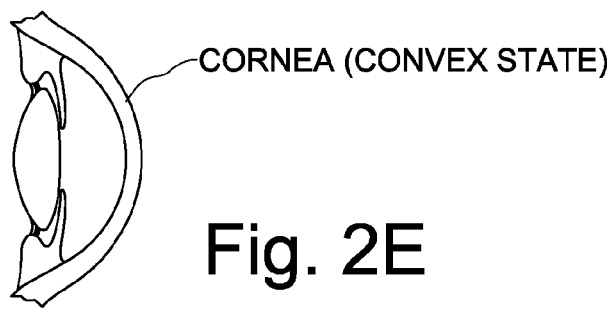

FIGS. 2A-2E show a corneal deformation cycle caused by the fluid pulse. FIG. 2A shows cornea C in its original and natural convex state. FIG. 2B shows cornea C in a first applanated (flattened) state as the cornea is pushed inwardly by the fluid pulse, and FIG. 2C shows cornea C in a concave state as the air pulse pushes the corneal tissue beyond its first applanated state of FIG. 2B. The air pulse then decays and the cornea is allowed to pass back through a second applanated state, shown in FIG. 2D, as the cornea deforms in an outward direction to return to its original and natural convex state depicted again in FIG. 2E. Thus, the fluid pulse causes a reversible deformation of cornea C characterized by first and second applanated states.

The corneal deformation cycle described above may be monitored by an optoelectronic monitoring system such as that shown in FIG. 1, wherein an emitter 26 such as an infra-red 26 is obliquely aimed at cornea C, and a photosensitive detector 28 is arranged on an opposite side of test axis TA to receive light from emitter 26 after it is reflected by cornea C. As will be understood, when cornea C is convex (FIGS. 2A, 2E) or concave (FIG. 2C), a substantially collimated beam from emitter 26 will become fanned out (divergent) after reflection by the curved corneal surface, and much of the light will not impinge upon photosensitive detector 28, such that the signal generated by photosensitive detector 28 will be relatively weak. However, when cornea C is in an applanated state (FIGS. 2B and 2D), the light beam from emitter 26 remains well-defined after reflection by the flattened corneal surface such that more light reaches photosensitive detector 28 and a peak signal is generated by the detector. The signal information generated by photosensitive detector 28 during the corneal deformation cycle, referred to herein as the "deformation signal," is processed by an amplifier and filter block 37 and converted to digital form by an analog-to-digital converter 38. The digital deformation signal, which comprises a set of data points each including an index or point number corresponding to a moment in time and a magnitude value representing a corresponding signal strength at that time, is input to main controller 40 and may be stored in memory 44.

Figure 3:
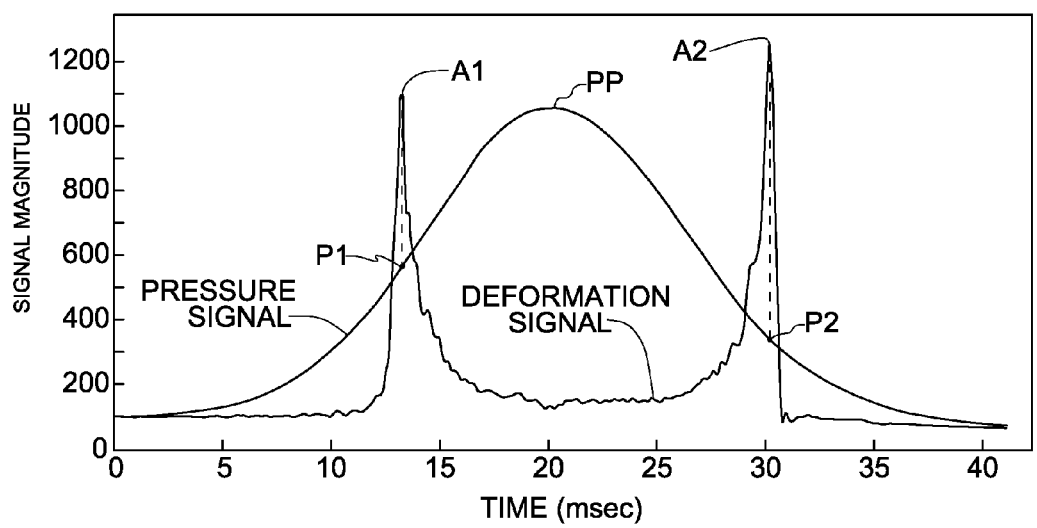
FIG. 3 is a plot showing a corneal deformation signal generated by the ophthalmic apparatus in the case of a normal eye, and a pressure signal superimposed on the deformation signal.

A deformation signal from a measurement of a normal eye (an eye without disease) is plotted in FIG. 3, and includes a pair of well-defined signal peaks A1 and A2 corresponding to the first applanated state of cornea C during inward deformation of the cornea (see FIG. 2B) and the second applanated state of cornea C during outward deformation of the cornea (see FIG. 2D), respectively. A deformation signal from a measurement an eye diagnosed as having keratoconus is plotted in FIG. 4. Keratoconus is a disease characterized by deterioration of the structure of the cornea with gradual bulging from the normal round shape to a cone shape. As may be observed by comparing FIGS. 3 and 4, the deformation signal associated with the keratoconic eye differs in appearance from the deformation signal associated with the healthy eye. As discussed more fully below, the deformation signal will vary in shape from eye-to-eye, and even from measurement-to-measurement for the same eye.

Figure 4:
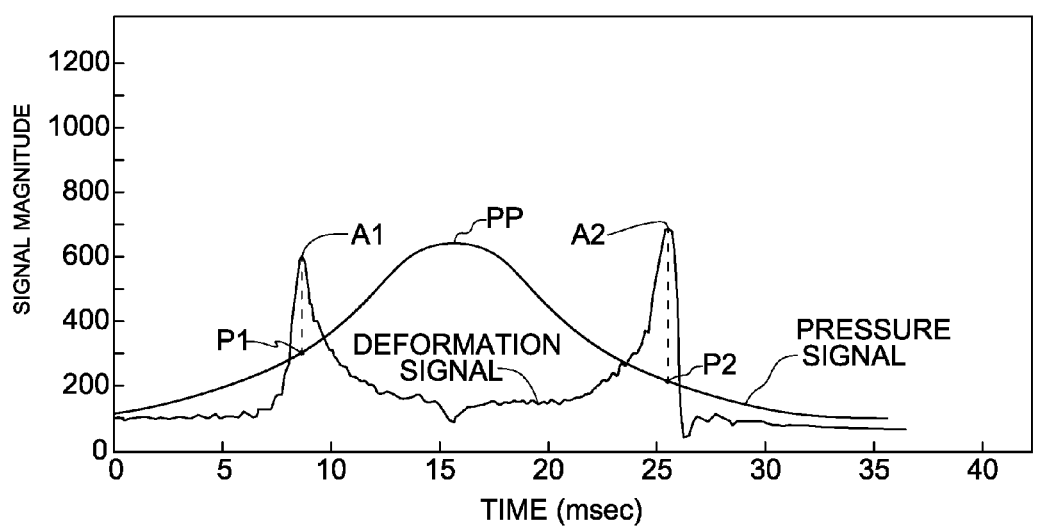
FIG. 4 is a plot showing a corneal deformation signal generated by the ophthalmic apparatus in the case of keratoconic eye.

The pressure within plenum chamber 17 is also monitored during the corneal deformation cycle. In the embodiment shown, a pressure sensor 22 is positioned in plenum chamber 17 near the entry end of fluid discharge tube 14 to generate signal information representative of the plenum pressure associated with the fluid pulse. The signal information generated by pressure sensor 22 is processed by an amplifier and filter block 36 and converted to digital form by analog-to-digital converter 38. The digital pressure signal, which comprises a set of data points each including an index or point number corresponding to a moment in time and a magnitude value representing a corresponding signal strength at that time, is input to main controller 40 and may be stored in memory 44. FIGS. 3 and 4 show the pressure signal superimposed with the associated deformation signal. The pressure signal is characterized by a Gaussian bell curve shape. It is preferable to adjust the parameters of pump mechanism 16 to provide a pressure signal that is at least approximately symmetrical about a moment in time and has a suitable spread, whereby a first pressure P1 coinciding with first applanation A1 and a second pressure P2 coinciding with second applanation A2 may be accurately determined by evaluating the deformation and pressure signals. For example, parameters that may be adjusted to optimize the shape of the pressure signal as a function of time include the weight of piston 18 and the time profile of the energizing current delivered by current source 34 to motor 20. Evaluation of the deformation signal and pressure signal is performed by main controller 40. If apparatus 10 is embodied as an NCT, the deformation and pressure signals may be evaluated for purposes of calculating an IOP measurement value.

The present invention recognizes that the deformation signal itself, beyond its usefulness in determining IOP, contains other information about the eye and about the physical measurement process that causes the corneal deformation cycle. Variability in the shape of the deformation signal among multiple measurements on the same eye is attributed primarily to differences in the physical measurement process, for example slight changes in gaze direction and/or alignment of the test axis with the cornea, and random blinking by the test subject. Variability in the shape of the deformation signal among measurements on a statistically large population of eyes is attributed primarily to differences in the properties of the eyes being measured, for example the topography and elasticity of the cornea, and of course IOP. Based on extensive experience in observing deformation signals obtained from various populations of eyes in a number of clinical NCT trials, applicant realized that the deformation signal has an ideal appearance associated with normal eyes subjected to a physical measurement process substantially as intended (i.e. with proper alignment of the test axis and minimal sources of error or noise in the measurement system). The present invention quantifies the extent to which a deformation signal has an ideal appearance.

In accordance with an embodiment of the present invention, main controller 40 includes a processing unit 41 programmed and configured to evaluate a measured deformation signal and calculate a deformation signal "score" for the measured deformation signal, wherein the deformation signal score represents a degree of probability that the deformation signal corresponds in shape to a normal deformation signal for a population of normal eyes. Processing unit 41 may be programmed by executable software instructions stored in memory 44.

The deformation signal score of the present invention provides an improved basis for weighing or discriminating between individual measurements on a particular eye. For example, the deformation signal score may be used to keep and/or discard certain measurements for use in calculating IOP. Instead of averaging multiple IOP values based on deformation signals from a series of measurements on an eye to yield a final IOP value, a single best deformation signal indicated by its deformation signal score may be chosen for calculation of IOP, and the remaining deformation signals from other measurements in the series may be discarded. Similarly, a single worst deformation signal may be discarded and the remaining deformation signals may be kept for computing an average IOP value. Of course, other schemes for keeping and/or discarding measurements based on the deformation signal score are possible.

Figure 5:
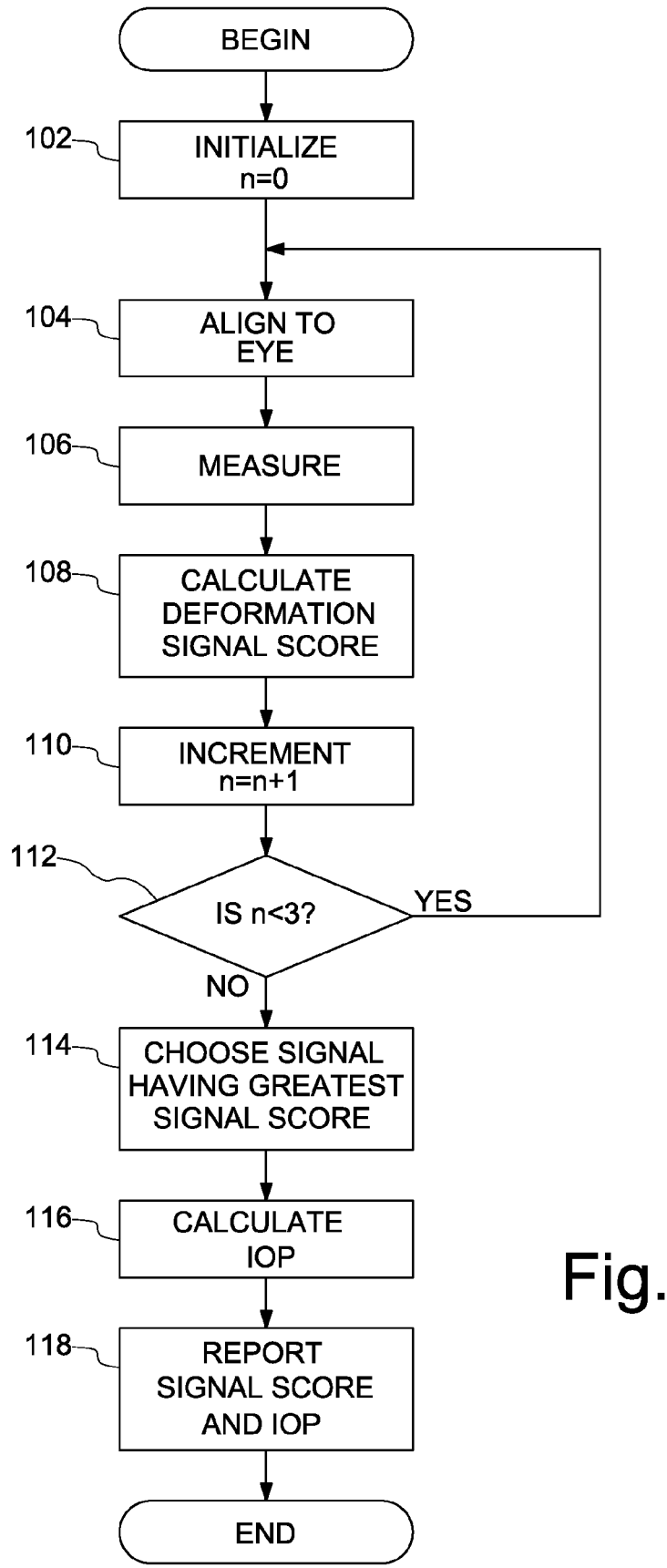
FIG. 5 is a flow chart generally illustrating a method of testing an eye in accordance with an embodiment of the present invention.

FIG. 5 illustrates, in a generalized manner, a method of testing an eye in accordance with an embodiment of the present invention. According to the method, a counter "n" for counting the number of measurements on the eye is initialized in block 102 by setting the counter value to zero. Then, discharge tube 14 is aligned to the eye in block 104 and pump mechanism 16 is triggered to carry out a measurement in accordance with block 106, wherein the measurement produces a deformation signal. Next, in block 108 and as described in detail below with reference to FIG. 6, a deformation signal score is calculated for the deformation signal obtained in block 106. Pursuant to blocks 110 and 112, counter "n" is increased by one and the counter value is compared to a predetermined total number of measurements to be made, which is three in this example embodiment (this step may be a carried out in the operator's head or automatically by the main controller 40). If the total number is not yet reached, then flow returns to block 104 to repeat the measurement procedure and obtain another deformation signal and corresponding deformation signal score. Once the predetermined number of measurements has been reached, flow proceeds to block 114, wherein the deformation signal having the greatest signal score is chosen from the plurality of deformation signals. The chosen deformation signal is used for calculating IOP in accordance with block 116. Finally, in block 118, the signal score and IOP value are reported by displaying and/or printing such results. A relatively low deformation signal score may serve as an indicator to the test provider that further diagnostic testing of the eye is warranted.

Figure 6:
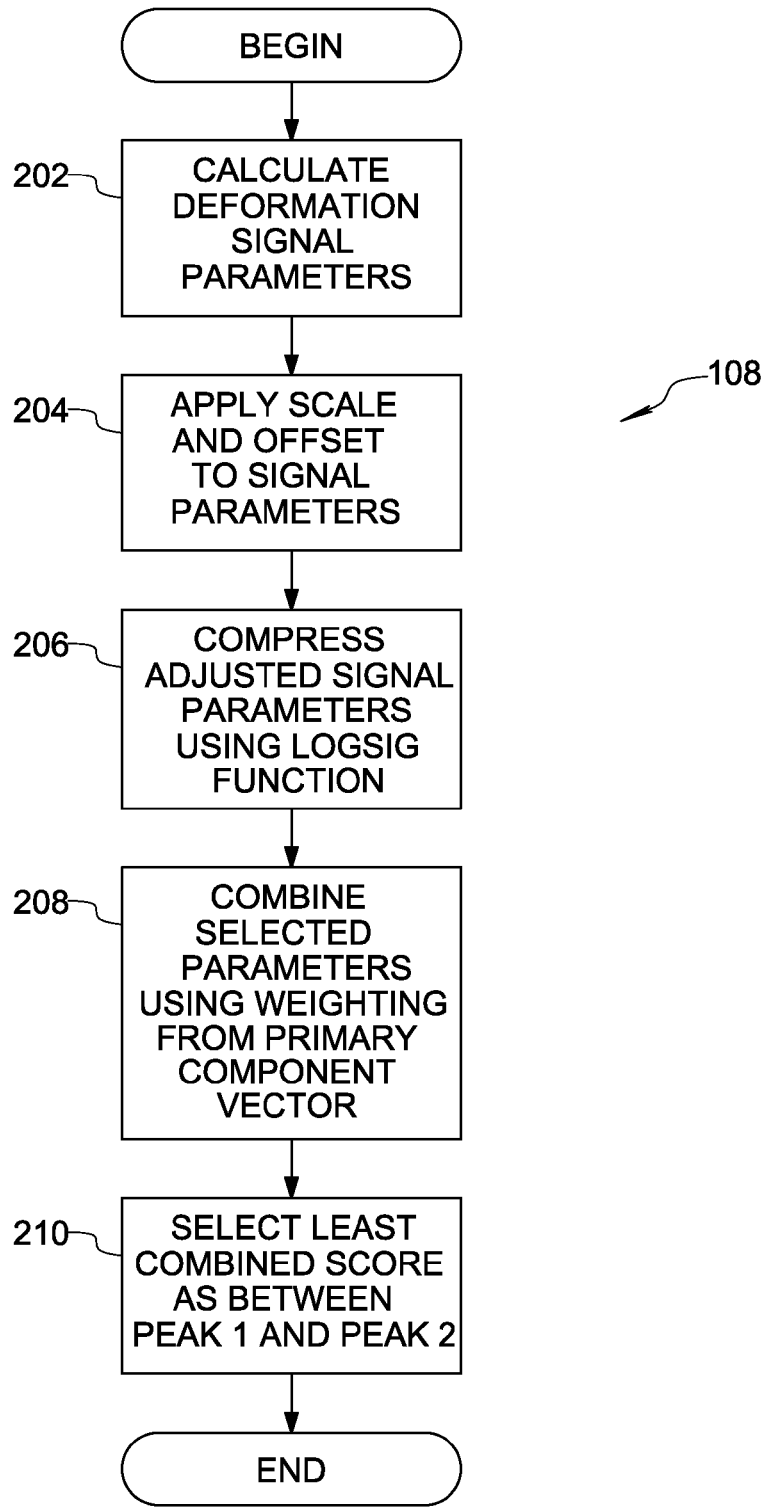
FIG. 6 is a flow chart illustrating how a deformation signal score may be calculated as part of the eye testing method of FIG. 5.

FIG. 6 illustrates calculation of the deformation signal score according to block 108 of FIG. 5 in greater detail. First, a set of selected signal parameters are calculated in block 202. Each of the signal parameters describes a respective geometrical property of the deformation signal. In an embodiment described herein, there are ten selected signal parameters in total, five of which are associated with first applanation peak A1 and five of which are associated with second applanation peak A2. As will become apparent from further description of the signal parameters given below, there are five different types of signal parameter, and each parameter type is determined for both first applanation peak A1 and second applanation peak A2. In order to divide the deformation signal into two portions corresponding to peaks A1 and A2, the deformation signal may be parsed about a moment in time corresponding to the peak pressure PP (FIG. 3) represented by the pressure signal.

The ten signal parameters used in the present embodiment were selected from a larger set of forty-two signal parameters based on a statistical principal components analysis of a large and diverse population of eyes including both normal and abnormal eyes. As will be described below in connection with FIG. 12, the principal components analysis provides a principal component vector consisting of a linear combination of five signal parameters that characterize a significant portion of the variability in the signal parameters obtained from the population of eyes. Each of the five signal parameters has an associated weighting given by the principal component vector. The five signal parameters identified through principal components analysis are applied to both first applanation peak A1 and second applanation peak A2, thereby providing ten signal parameters in total.

Each of the signal parameters will now be described with reference to FIGS. 7-11.

Figure 7:
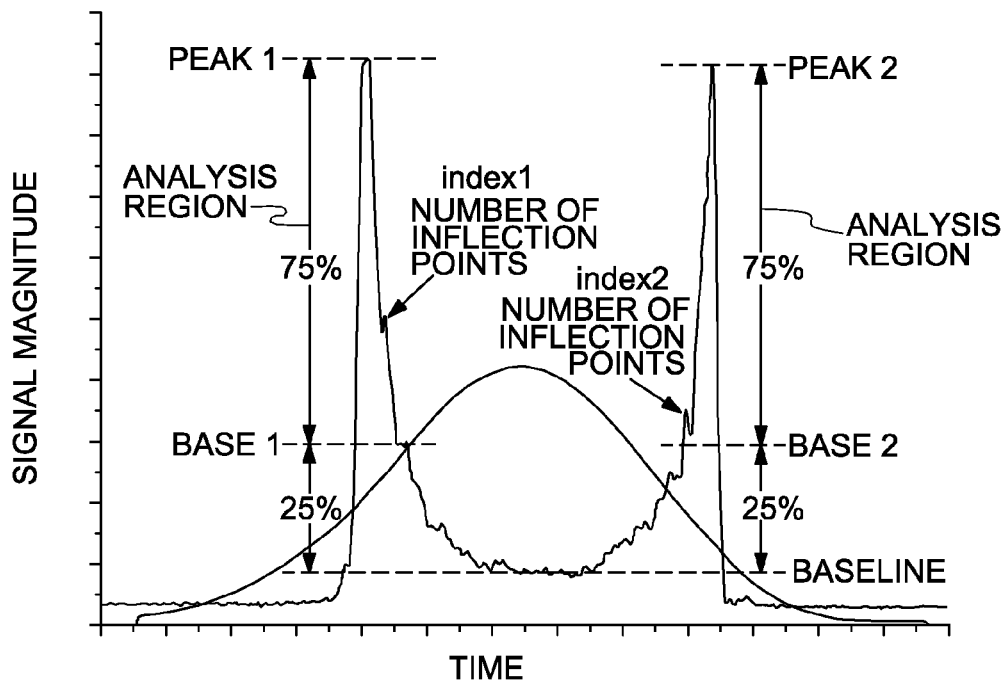
FIG. 7 is a plot of a corneal deformation signal, illustrating signal parameters (index1, index2) describing smoothness of first and second deformation signal peaks.

FIG. 7 illustrates parameters index1 and index2 describing a smoothness of the first and second signal peaks, respectively. The index1, index2 parameters represent the number of inflection points in the signal peak (i.e. the number of times the signal changes direction) within an analysis region of the signal peak. An analysis region is defined to exclude signal activity during periods not closely associated with corneal applanation. In the example described in the present specification, the analysis region is defined for each peak as the upper 75% of the peak as measured from the BASELINE between peaks to the top or maximum of the peak. Thus, in the present example, the analysis region for the first signal peak extends from BASE-1 to PEAK-1, and the analysis region for the second signal peak extends from BASE-2 to PEAK-2. Other analysis regions may be defined without straying from the invention.

Figure 8:
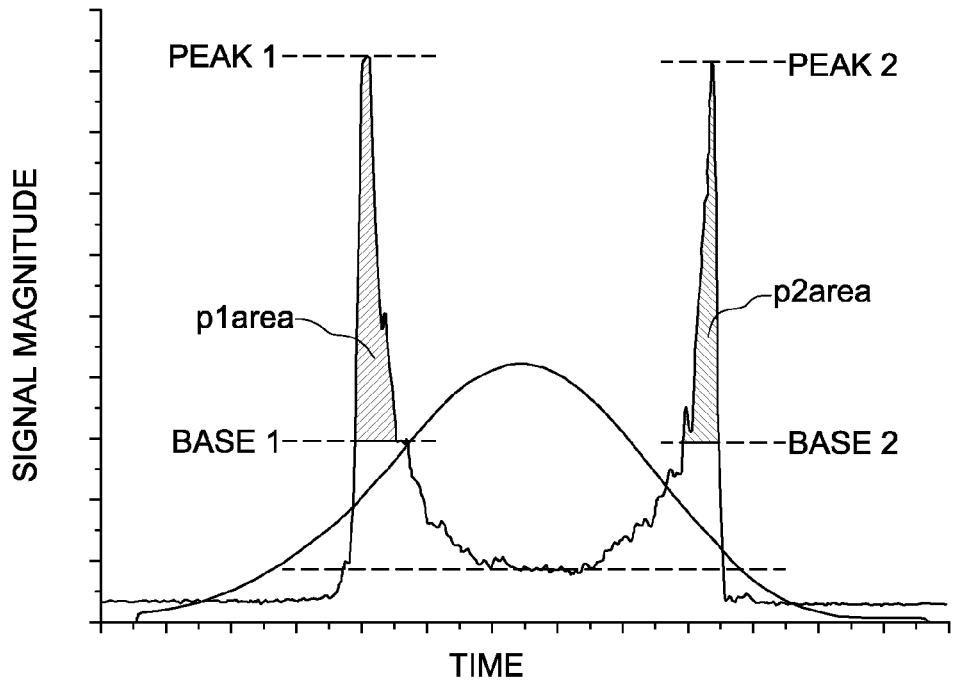
FIG. 8 is a plot of a corneal deformation signal, illustrating signal parameters (areap1, areap2) describing an area under first and second deformation signal peaks.

FIG. 8 depicts parameters p1area and p2area describing an area under the first and second signal peaks, respectively. The same analysis regions may be used, with the BASE-1 and BASE-2 lines each serving as part of an area definition boundary for the associated area parameter.

Figure 9:
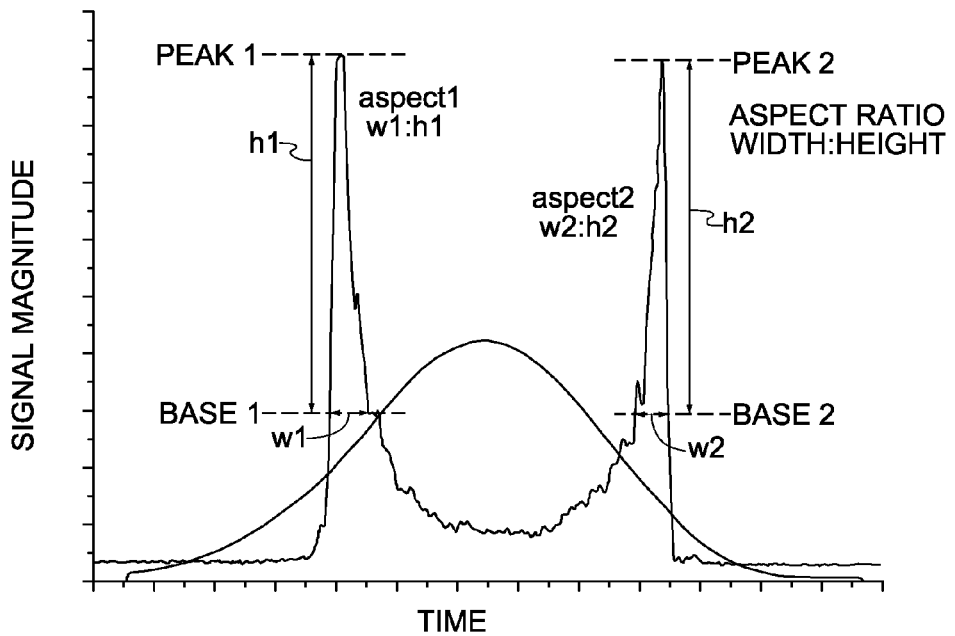
FIG. 9 is a plot of a corneal deformation signal, illustrating a signal parameters (aspect1, aspect2) describing an aspect ratio of first and second deformation signal peaks.

Parameters aspect1, aspect2 are illustrated in FIG. 9. These describe an aspect ratio of the associated signal peak, defined as the ratio of a width of the peak (w1 or w2) to the height of the peak (h1 or h2). Again, the same analysis regions may be adopted.

Figure 10:
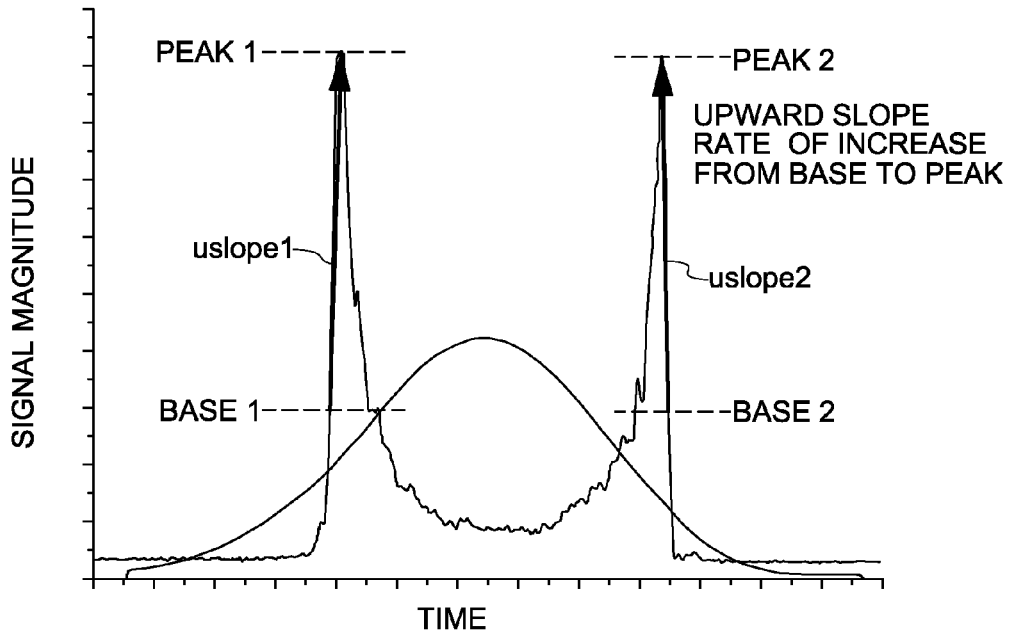
FIG. 10 is a plot of a corneal deformation signal, illustrating a signal parameters (uslope1, uslope2) describing an upward slope of first and second deformation signal peaks.

FIG. 10 shows parameters uslope1, uslope2 describing an upward slope of the associated signal peak from BASE to PEAK. As may be seen, uslope2 is measured in a reverse time direction because the applanation event giving rise to the second signal peak is time reversed relative to the first applanation event (the cornea is returning to its original convex state). The same analysis regions may be used.

Figure 11:
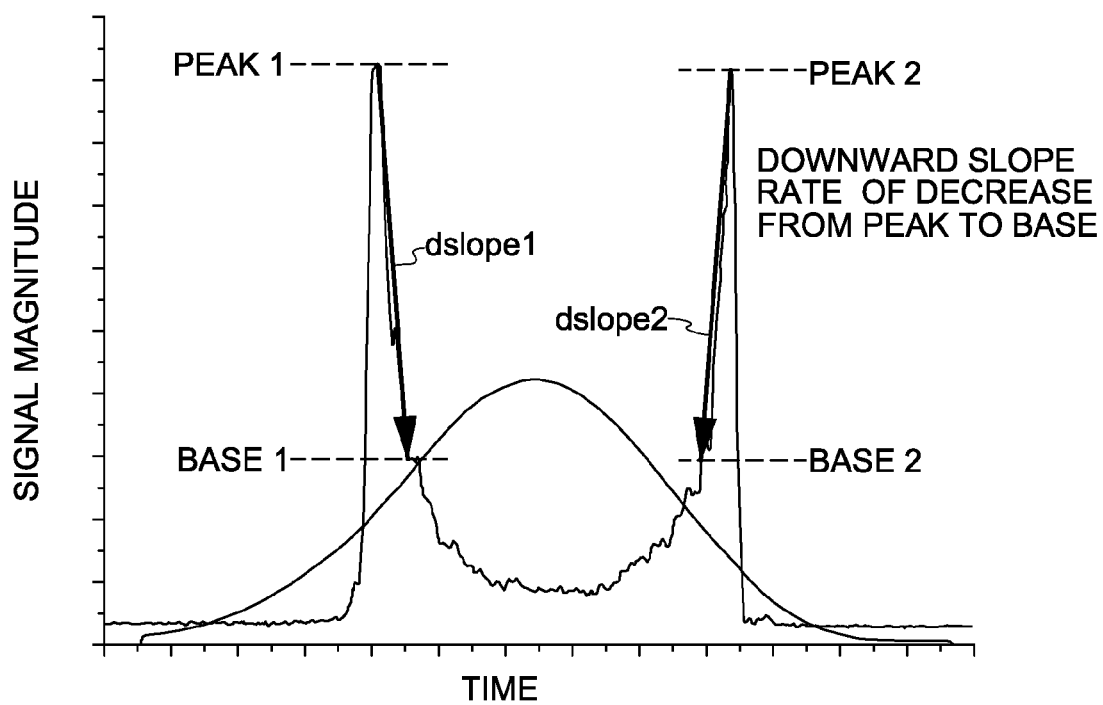
FIG. 11 is a plot of a corneal deformation signal, illustrating a signal parameters (dslope1, dslope2) describing a downward slope of first and second deformation signal peaks.

FIG. 11 depicts parameters dslope1 and dslope2, which are similar to parameters uslope1 and uslope2 except they describe a downward slope of the associated signal peak. As with parameter uslope2, parameter dslope2 is measured in reverse time direction as can be seen in FIG. 11. The same analysis regions may again be adopted for the two signal peaks.

Returning to FIG. 6, after the deformation signal parameters are calculated in block 202, a scaling factor and an offset are applied to each signal parameter in block 204 resulting in a set of adjusted signal parameters. In the present embodiment, the scaling factor and offset applicable to a given signal parameter are chosen such that when each adjusted signal parameter is compressed in accordance with subsequent block 206, the compressed signal parameter value will be within a predetermined numerical range, for example 0-10. Compression of the adjusted signal parameters may be performed using a LOGSIG transfer function and multiplier, for example 10*LOGSIG(adjusted_parameter). Thus, in the present embodiment, each of the ten compressed parameters will have a value ranging from 0-10. It is noted that a different predetermined numerical range and compression multiplier may be chosen without straying from the present invention.

Once the adjusted signal parameters have been compressed such that each compressed parameter has a value in the predetermined numerical range, the five parameters for a given peak are combined in block 208 in accordance with parameter weighting factors given by the principal components analysis mentioned above. For example, if the principal component vector is [0.3211 0.3086 0.5706 0.4288 0.5404] for parameters (index1, p1area, aspect1, uslope1, dslope1) describing the first peak, then the compressed parameters (index1$_c$, p1area$_c$, aspect1$_c$, uslope1$_c$, dslope1$_c$) each in the range 0-10 are combined as follows:

$$\frac{0.3211 * index1_c + 0.3086 * p1area_c + 0.5706 * aspect1_c + 0.4288 * uslope_c + 0.5404 * dslope_c}{2.1695}$$

to yield a composite score in the range 0-10 for the first peak. The compressed parameters describing the second peak may be combined in the same way to yield a composite score in the range 0-10 for the second peak. Finally, pursuant to step 210, the least composite score as between the first peak composite score and the second peak composite score is selected and returned as an overall "deformation signal score." As may be understood from the foregoing description, the deformation signal score indicates a degree of probability that the deformation signal corresponds in shape to a normal deformation signal for a population of normal eyes.

Figure 12:
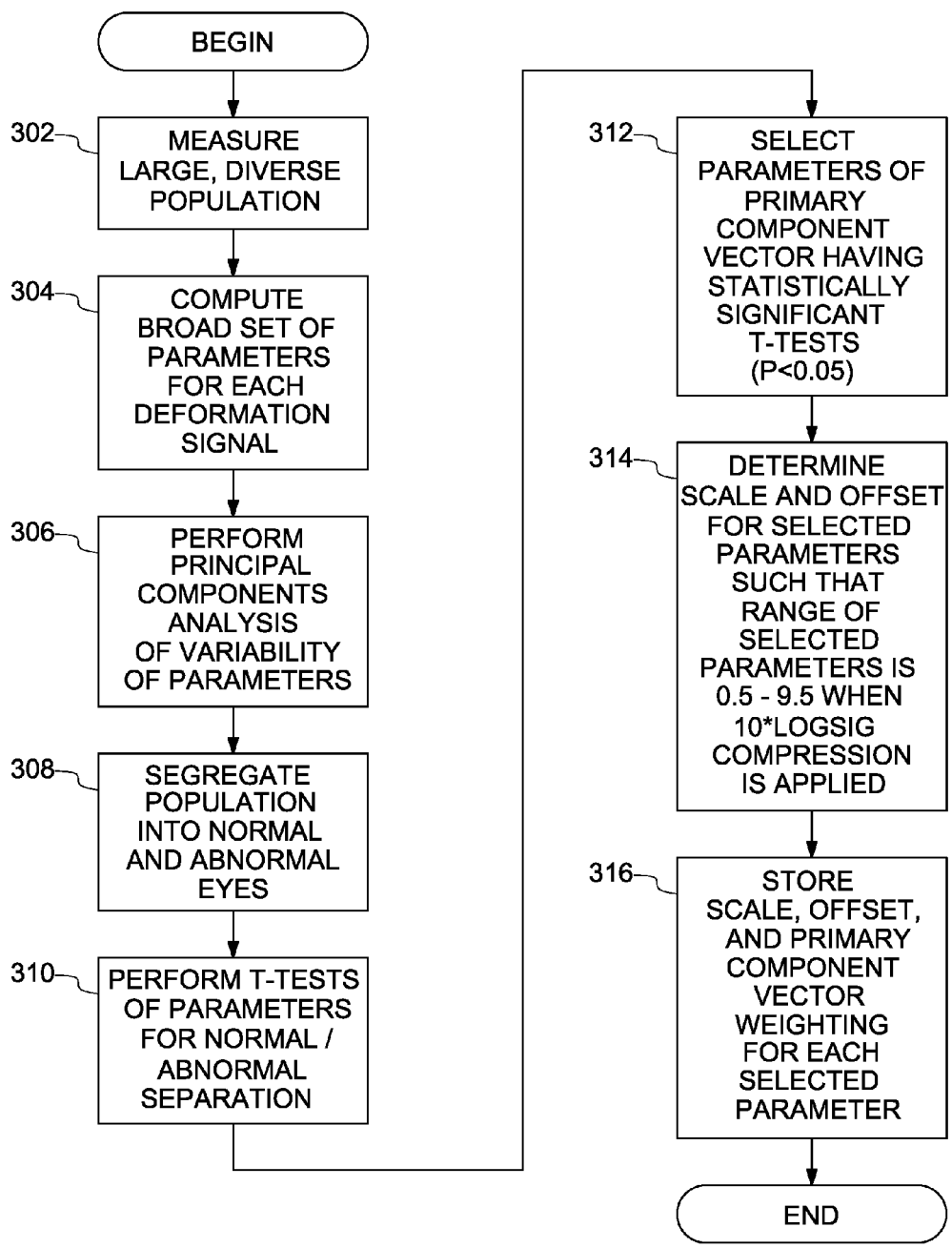
FIG. 12 is a flow chart showing a process for selecting the signal parameters illustrated in FIGS. 7-11 and determining their respective weightings in calculating the deformation signal score in accordance with FIG. 6.

FIG. 12 illustrates the methodology leading to the selection of the signal parameters described above and their weighting when combined to calculate the deformation signal score. In block 302, deformation and pressure signals were obtained for a large and diverse population of eyes. In the context of the present specification, "diverse" means that the population of eyes includes eyes diagnosed as normal or healthy, and also eyes diagnosed as abnormal or having disease. In block 304, a broad set of signal parameters was computed. By way of non-limiting example, forty-two different signal parameters were calculated for the deformation signal, some parameters being dependent on the relationship between the pressure signal and the deformation signal, and some parameters describing a respective geometrical property of the deformation signal itself, without reference to the pressure signal. The ten signal parameters described above fall into the latter category, and each is associated either with the first peak or the second peak of the deformation signal.

Once the broad set of signal parameters were computed for each deformation signal in the population, variability among the signal parameters was analyzed to identify those parameters which contribute most to the signal parameters' variabilities. For this purpose, a statistical "principal components analysis" of the signal parameters was performed. Computer software, e.g. MATLAB® from The MathWorks, Inc., is available for performing a principal components analysis on the collected signal parameter data. Principal components analysis removes redundancy by complex multidimensional correlation analysis and is a standard procedure for consolidating/removing redundancy in large data sets. The output from principal components analysis is a number of approximately orthogonal vectors that characterize the overall variability of the parameter data. The number of vectors generated by the analysis is determined by specifying at the beginning of the process how much (what percentage) of the total variability one wishes to characterize. In the present example, 98% was specified as an input condition for the principal components analysis. Five vectors resulted to characterize the variability of each deformation signal peak, wherein each vector is a linear combination of a subset of the original forty-two signal parameters.

The first (or primary) principal component vector consisted of a linear combination of five parameters. For the first signal peak, the five parameters of the principal component vector were (index1, p1area, aspect1, uslope1, dslope1) having a corresponding weighting of [0.3211 0.3086 0.5706 0.4288 0.5404]. Analogous signal parameters (index2, p2area, aspect2, uslope2, dslope2) were identified for the second peak and had a substantially similar weighting. The primary component vector represented 76% of the total variability, with the next component representing only 7%. Therefore, only the primary component vector was used, without significant loss of information.

Blocks 308, 310, and 312 are procedural steps taken to confirm that variability in the parameters of the primary component vector is not likely to have been due to chance. In block 308, the population signal data was segregated into normal and abnormal categories based on an independent clinical diagnosis made with respect to each measured eye. Within each category (normal or abnormal), each parameter had a generally Gaussian distribution. Statistical t-tests were performed on the normal and abnormal parameter distributions for each parameter in the primary component vector as indicated by block 310, and those parameters having a statistically significant t-test (e.g. an alpha level or risk level less than 0.05) were selected according to block 312. In the example described herein, all primary component parameters had statistically significant t-tests.

As indicated by blocks 204 and 206 in FIG. 6, the signal parameters are scaled and compressed before being combined to calculate the overall deformation signal score. Accordingly, in block 314 of FIG. 12, a scale factor and offset value were determined for adjusting each selected parameter such that the range of each parameter was 0.5-9.5 when a 10*LogSig compression was applied to each adjusted parameter. Finally, in block 316, the scale factor, offset value, and primary component vector weightings (e.g. [0.3211 0.3086 0.5706 0.4288 0.5404]) were stored in memory 44.

As a result of the process shown in FIG. 12, the scale factor, offset value, and weighting values necessary for blocks 204, 206, and 208 of FIG. 6 were derived and stored. It will be understood that the actual scale factor, offset value, and weighting values are specific to the type of instrument used to measure the eye and generate the deformation signal data, and will depend on the physical and operational characteristics thereof. In the example described herein, the OCULAR RESPONSE ANALYZER® instrument (also known by the acronym ORA) manufactured by Reichert, Inc., assignee of the present invention, was used.

While the invention has been described in connection with an exemplary embodiment, the detailed description is not intended to limit the scope of the invention to the particular forms set forth. The invention is intended to cover such alternatives, modifications, and equivalents of the described embodiment as may be included within the spirit and scope of the invention.

What is claimed is:

1. An ophthalmic apparatus for testing an eye of a patient, the apparatus comprising:
a fluid pump operable to generate a fluid pulse for deforming a cornea of the eye from an original convex state through a first applanated state to a concave state, wherein the cornea returns from the concave state through a second applanated state to the original convex state;
a deformation detection system including a emitter and a photosensitive detector, the detector receiving light from the emitter after the light is reflected by the cornea and generating a deformation signal representative of corneal deformation associated with the fluid pulse as a function of time;
signal processing electronics that converts the deformation signal from analog to digital form; and
a processing unit receiving the deformation signal in digital form, wherein the processing unit is programmed to calculate a deformation signal score indicating a degree of probability that the shape of the deformation signal over time corresponds to the shape of a normal deformation signal for a population of normal eyes;
wherein the deformation signal score provides a basis to keep or discard an intraocular pressure measurement in a non-contact tonometer or a basis for conducting further diagnostic screening.

2. The apparatus according to claim 1, wherein the deformation signal score is calculated by combining a plurality of signal parameters calculated by the processing unit, each signal parameter describing a respective geometrical property of the deformation signal.

3. The apparatus according to claim 2, wherein the deformation signal has a shape characterized by a first signal peak corresponding to the first applanated state and a second signal peak corresponding to the second applanated state, and the plurality of signal parameters includes at least one set of signal parameters selected from a first set of signal parameters describing respective geometrical properties associated with the first signal peak and a second set of signal parameters describing respective geometrical properties associated with the second signal peak.

4. The apparatus according to claim 2, wherein the plurality of signal parameters are selected from a larger plurality of signal parameters based on a principal components analysis of deformation signals obtained from a population of eyes.

5. The apparatus according to claim 4, wherein the signal parameters are weighted according to a principal component vector derived from the principal components analysis in calculating the deformation signal score.

6. The apparatus according to claim 3, wherein the first set of signal parameters and the second set of signal parameters each include at least one parameter selected from a group of parameters consisting of: a parameter describing a smoothness of the associated signal peak, a parameter describing an area under the associated signal peak, a parameter describing an aspect ratio of the associated signal peak, a parameter describing an upward slope of the associated signal peak, and a parameter describing a downward slope of the associated signal peak.

7. The apparatus according to claim 6, wherein the first set of signal parameters and the second set of signal parameters each include all five of the parameters in the group of parameters.

8. A method of testing an eye comprising the steps of:
reversibly deforming the cornea of the eye from an original convex state through a first applanated state to a concave state by directing a fluid pulse through a fluid discharge tube at the cornea, wherein the cornea returns from the concave state through a second applanated state to the original convex state;

generating a deformation signal representative of the corneal deformation as a function of time; and calculating a deformation signal score indicating a degree of probability that the shape of the generated deformation signal corresponds in over time corresponds to the shape of a normal deformation signal over time for a population of normal eyes;

wherein the deformation signal score provides a basis to keep or discard an intraocular pressure measurement in a non-contact tonometer or a basis for conducting further diagnostic screening.

9. The method according to claim 8, further comprising the step of reporting the deformation signal score.

10. The method according to claim 8, wherein the method is performed a plurality of times in conjunction with measuring intraocular pressure of the eye such that a plurality of deformation signals are generated each having a respective deformation signal score, wherein at least one of the plurality of deformation signals is kept or discarded based on the corresponding deformation signal score of such deformation signal.

11. The method according to claim 10, wherein a deformation signal chosen from the plurality of deformation signals as having the greatest deformation signal score is kept for use in measuring intraocular pressure and any remaining deformation signals in the plurality of deformation signals are discarded.

12. The method according to claim 8, wherein the step of calculating the deformation signal score includes calculating a plurality of signal parameters, each signal parameter describing a respective geometrical property of the deformation signal.

13. The method according to claim 12, wherein the deformation signal has a shape characterized by a first signal peak corresponding to the first applanated state and a second signal peak corresponding to the second applanated state, and the plurality of signal parameters includes at least one set of signal parameters selected from a first set of signal parameters describing respective geometrical properties associated with the first signal peak and a second set of signal parameters describing respective geometrical properties associated with the second signal peak.

14. The method according to claim 13, wherein the first set of signal parameters and the second set of signal parameters each include at least one parameter selected from the group of parameters consisting of: a parameter describing a smoothness of the associated signal peak, a parameter describing an area under the associated signal peak, a parameter describing an aspect ratio of the associated signal peak, a parameter describing an upward slope of the associated signal peak, and a parameter describing a downward slope of the associated signal peak.

15. The method according to claim 14, wherein the first set of signal parameters and the second set of signal parameters each include all five of the parameters in the group of parameters.

16. In a non-contact tonometer for measuring intraocular pressure by directing a fluid pulse through a fluid discharge tube at a cornea and analyzing a corneal deformation signal captured during reversible deformation of the cornea from an original convex state through a first applanated state to a concave state, wherein the cornea returns from the concave state through a second applanated state to the original convex state, the improvement comprising:

a processing unit programmed and configured to calculate a deformation signal score indicating a degree of probability that the shape of the deformation signal over time corresponds to the shape to a normal deformation signal over time for a population of normal eyes;

wherein the deformation signal score provides a basis to keep or discard an intraocular pressure measurement in a non-contact tonometer or a basis for conducting further diagnostic screening.

17. The improvement according to claim 16, wherein the deformation signal score is calculated for each of a plurality of measurements on the eye to provide a plurality of scored deformation signals, and at least one of the plurality of scored deformation signals is kept or discarded based on the corresponding deformation signal score of such deformation signal.

18. The improvement according to claim 17, wherein one of the plurality of measurements having the greatest deformation signal score is kept for use in measuring intraocular pressure, and any remaining deformation signals in the plurality of scored deformation signals are discarded.

* * * * *